(12) United States Patent
Seeram et al.

(10) Patent No.: US 7,638,640 B2
(45) Date of Patent: Dec. 29, 2009

(54) PURIFICATIONS OF POMEGRANATE ELLAGITANNINS AND THEIR USES THEREOF

(75) Inventors: Navindra P. Seeram, Los Angeles, CA (US); David Heber, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/395,447

(22) Filed: Mar. 30, 2006

(65) Prior Publication Data

US 2006/0211635 A1 Sep. 21, 2006

Related U.S. Application Data

(63) Continuation-in-part of application No. PCT/US2005/009337, filed on Mar. 21, 2005.

(60) Provisional application No. 60/556,322, filed on Mar. 24, 2004.

(51) Int. Cl.
C07D 493/00 (2006.01)
A01K 43/04 (2006.01)
A01N 43/42 (2006.01)
A01N 43/16 (2006.01)

(52) U.S. Cl. ............... 549/278; 514/292; 514/453; 514/456; 514/27

(58) Field of Classification Search ........... 549/278; 514/27, 292, 453, 456
See application file for complete search history.

(56) References Cited

U.S. PATENT DOCUMENTS 6,387,418 B1 * 5/2002 Aviram et al. ............ 424/744
6,641,850 B1 * 11/2003 Aviram et al. ............ 424/769
6,977,089 B1 * 12/2005 Aviram et al. ............ 424/769

FOREIGN PATENT DOCUMENTS

JP 61100517 A * 10/1984

OTHER PUBLICATIONS

Gil et al. Journal of Agricultural and Food Chemistry, 2000, 48, 4581-4589.*
Mayer et al. Liebigs Annalen der Chemie 1977, 1976-1986.*
Cerda et al. Journal of Agricultural and Food Chemistry, 2003, 51, 3493-3501.*
Mayer, W., et al., "Punicalagin und punicalin, zwei gerbstoffe aus den scalen der granatapfel," (1977) Liebigs Ann. Chem., 1976-1986 (in German with English language abstract).
Aviram, M., et al., "Pomegranate juice consumption inhibits serum angiotensin converting enzyme activity and reduces systolic blood pressure," (2001) *Atherosclerosis*, 158:195-198.
Cerdá, B., et al., "Evaluation of bioavailability and metabolism in the rat of punicalagin, an antioxidant polyphenol from pomegranate juice," (2003) *Eur. J. Nutr.*, 42:18-28.
Cerdá, B., et al., "Repeated oral administration of high doses of the pomegranate ellagitannin punicalagin to rats for 37 days is not toxic," (2003) *J. Agric. Food Chem.*, 51:3493-3501.
Doig, A., et al., "Isolation and structure elucidation of punicalagin, a toxic hydrolysable tannin, from *Terminalia oblongata*," (1990) *J. Chem. Soc. Perkin Trans. I*, 2317-2321.
El-Toumy, S., et al., "Two ellagitannins from *Punica granatum* heartwood," (2002) *Phytochemistry*, 61:971-974.
Filippich, L., et al., "Hepatotoxic and nephrotoxic principles in *Terminalia oblongata*," (1991) *Research in Veterinary Science*, 50:170-177.
Gil, M., et al., "Antioxidant activity of pomegranate juice and its relationship with phenolic composition and processing," (2000) *J. Agric. Food Chem.*, 48:4581-4589.
Negi, P., et al., "Antioxidant and antimutagenic activities of pomegranate peel extracts," (2003) *Food Chemistry*, 80:393-397.
Scalbert, A., et al., "Absorption and metabolism of polyphenols in the gut and impact on health," (2002) *Biomed. Pharmacother.*, 56:276-282.
Tanaka, T., et al., "Tannins and related compounds. XL. Revision of the structures of punicalin and punicalagin, and isolation and characterization of 2-O-Galloylpunacalin from the bark of *Punica granatum* L." (1986) *Chem. Pharm. Bull.*, 34(2):650-655.
Tanaka, T., et al., "Tannins and related compounds. XLL. Isolation and characterization of novel ellagitannins, punicacorteins A, B, C and D, and punigluconin from the bark of *Punica granatum* L.," (1986) *Chem. Pharm. Bull.*, 34(2):656-663.
Vidal, A., et al., "Studies on the toxicity of *Punica granatum* L. (Punicaceae) whole fruit extracts," (2003) *Journal of Ethnopharmacology*, 89:295-300.
Tanaka; et al., "Punicafolin, an Ellagitannin from the Leaves of *Punica granatum*", Phytochemistry (1985), 24 (9):2075-2078.

* cited by examiner

*Primary Examiner*—D. Margaret Seaman
*Assistant Examiner*—Nizal S Chandrakumar
(74) *Attorney, Agent, or Firm*—Bozicevic Field & Francis LLP; Pamela J. Sherwood

(57) ABSTRACT

Compositions of purified and biologically active ellagitannins are provided by separation from pomegranate husk using a method of extraction and purification using a solid polymeric adsorbent and the uses of the said compounds.

21 Claims, 4 Drawing Sheets

US 7,638,640 B2

PURIFICATIONS OF POMEGRANATE ELLAGITANNINS AND THEIR USES THEREOF

GOVERNMENT RIGHTS

This invention was made with Government support of Grant No. PS0AT00151 awarded by the National Institutes of Health. The Government has certain rights in this invention.

INTRODUCTION

Recent research has shown that pomegranate (*Punica granatum* L.) juice and pomegranate extracts exhibit potent biological properties attributable to the presence of polyphenols known as ellagitannins. These hydrolysable tannins are present in high levels in pomegranates and include punicalagin anomers commonly referred to as punicalagins punicalin gallagic acid and ellagic acid Pomegranate ellagitannins have been identified as the active antioxidant compounds responsible for protecting low-density lipoprotein cholesterol from oxidation in vivo, a key step in the pathogenesis of atherosclerosis. The punicalagins are key compounds responsible for the antioxidant properties of pomegranate extracts. However, research has shown that the synergistic combination of punicalagins with other minor pomegranate ellagitannins, specifically punicalin and gallagic acid, results in superior biological activities. Unfortunately, there are no methods currently available for rapid and large scale production of these minor pomegranate ellagitannins. This invention proposes a method to produce ellagitannins from pomegranates and outlines their uses.

Current studies on ellagitannins include antioxidant properties, anticancer potential, the inhibition of COX-1 and COX-2 enzymes; anti-athersclerotic activity; inhibition of the nuclear transcription factor NF-κB, repression of glutathione expression, and anti-adhesion effects; and the like.

Punicalagin is the predominant pomegranate ellagitannin (present in levels >2 g/L in commercial pomegranate juice), and is responsible for the high antioxidant activity of pomegranate juice. However, little is known about the biological properties, bioavailability and metabolism of other pomegranate ellagitannins such as gallagic acid.

Previous methods of isolating pomegranate ellagitannins include time consuming preparative high-performance liquid chromatographic (HPLC) and/or column chromatographic) methods. In view of the commercial interest in these compounds, the development of inexpensive, high throughput methods of purifications of particular interest.

SUMMARY OF THE INVENTION

Compositions of purified and biologically active ellagitannins, specifically including punicalagin and gallagic acid are provided, as well as methods for producing such compositions and their uses. Ellagitannins are separated from other pomegranate natural products by a method of extraction and purification using a series of solvent-solvent extractions and chromatography with solid polymeric adsorbents. Included in the compositions of the invention are extracts comprising gallagic acid at a concentration of at least about 0.1% or more, up to substantially pure gallagic acid. Also included in the compositions of the invention are extracts comprising punicalagin at a concentration of at least about 0.1% or more, up to substantially pure punicalagin. Compositions are also provided comprising ellagic acid and ellagic acid glycosides at a concentration of at least about 5% or more. In another embodiment, compositions are provided comprising anthocyanins and anthocyanidins at a concentration of at least about 0.1%, about 5%, or more. Extracts comprising these compounds, and extracts comprising total pomegranate tannins, are useful for a variety of applications, including pharmaceutical, neutraceutical, cosmetic, and food uses.

In one embodiment of the invention, dried pomegranate peels are ground and suspended with an alcohol such as methanol. A rapid polymeric adsorbent column is used to purify pomegranate tannins from an aqueous or alcoholic extract, which extract is derived from a source of ellagitannins such as a variety of plant extracts, including *Punica granatum* L, and the like. The tannins are adsorbed to the columns, and followed by cleansing, gravity evacuation, and vacuum aspiration of fluid from the column, the adsorbed tannins are eluted from the adsorbent solid and the solvent removed in vacuo to yield a powder of highly concentrated total tannins comprising a high percentage (e.g., 80%) of punicalagin anomers, as well as a significant percentage of ellagic acid. Additional chromatography steps may be performed to provide for highly purified compositions of gallagic acid or punicalagin.

The present invention also provides a method for producing a mixture comprising ellagitannins from pomegranate. The method may include the use of enzymes such as extractase and pectinase. The method may include the steps of providing an aqueous solution containing the ellagitannins from the pomegranate; removing the ellagitannins onto a resin surface from the aqueous solution; eluting the resin surface with a eluant to remove the ellagitannins from the resin surface; and separating the eluant from the ellagitannins. The starting material may be fresh, or quick frozen and thawed. The material is then disrupted, and the ellagitannins extracted from the pulp into an aqueous solution.

The extracts thus obtained may be used in the preparation of tinctures, cosmetics and other therapeutic formulae, as food biopreservatives, in the nutraceutical industry; and the like. The compositions also find use as a source of ellagic acid derivatives, including hydrolysable ellagitannins, for use in in vitro and in vivo biological studies. The compounds thus isolated are reported to have antioxidant and anti-inflammatory activity.

DESCRIPTION OF THE SPECIFIC EMBODIMENTS

Figure 1A:
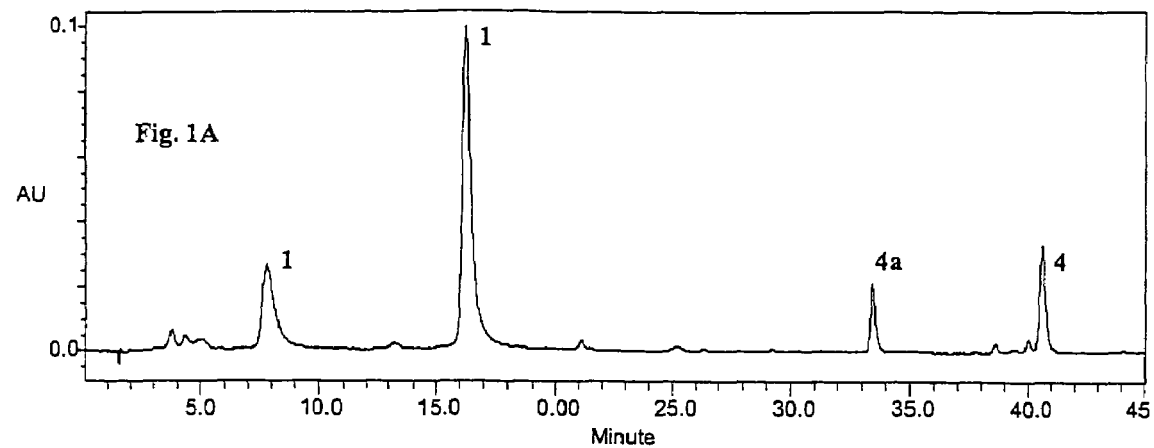
FIG. 1A: HPLC chromatogram of total pomegranate tannins (TPT) purified from fruit husk. Peaks were identified by comparison of their retention times with pure standards as punicalagin anomers (1) and ellagic acid (4), corresponding to m/z 1083 and m/z 301 in LCMS, respectively. Peak 4a was identified as ellagic acid hexoside based on its ion at m/z 463 as previously reported.

Polymeric adsorbent resins are used to purify tannins from an aqueous pomegranate extract. After adsorption, the resins are subjected to cleansing, gravity evacuation, and vacuum aspiration of fluid. The adsorbed tannins are then eluted from the resins and the solvent removed in vacuo to yield a powder of highly concentrated total tannins, which may comprise a high level of ellagitannins, including, for example, gallagic acid, punicalagins, punicalin, ellagic acid; ellagic acid glycosides; anthocyanins and anthocyanidins; etc.

The extracts thus obtained may be used in biological studies, for pharmaceutical uses; in the preparation of tinctures, cosmetics and other therapeutic formulae, as food additives, in the nutraceutical industry; and the like. The isolated mixtures of ellagitannins can also be tableted or used as capsules, soft gels and the likes and used as a natural nutraceutical/dietary supplement. In general, the tablets, capsules, soft gels etc. provide a daily dose of the tannins. The amount of the ellagitannins can be adjusted by isolating the individual compounds and blending them-together. The tablets capsules, soft gels etc may comprise the natural mixture of the ellagitannins that are isolated by the resin.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Purification of Ellagitannins

Compositions enriched in ellagitannins are recovered from plant material, which plant material may include husks, juice, leaves, woody stems, and the like. Plants suitable for extraction include husks of *Punica granatum*.

A suspension of material from the plant material is prepared by a variety of methods as known in the art, e.g. blending, aqueous extraction, etc. The plant material may be subjected to enzymatic treatment including but not limited extractase, pectinase and the likes. The aqueous solution comprising ellagitannins is applied to a polymeric adsorbent column, which is then washed with an aqueous buffer to remove unbound material. The tannins of interest bind to the resin, and may be eluted with a polar solvent, e.g. water, ethanol, methanol, acetone, etc.

The resin has a surface to which the ellagitannins are adsorbed. A preferred class of adsorptive resins are polymeric crosslinked resins composed of styrene and divinylbenzene such as, for example, the AMBERLITE series of resins, e.g. AMBERLITE XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322 manufactured by The Dow Chemical Company, Midland, Mich., and the like.

It is preferred to use commercially available, FDA-approved, styrene-divinyl-benzene (SDVB) cross-linked copolymer resin, (e.g., AMBERLITE XAD-16). Thus, in one embodiment, AMBERLITE XAD-16, commercially available from Rohm and Haas Company, and described in U.S. Pat. No. 4,297,220, herein incorporated by reference, is used as the resin. This resin is a non-ionic hydrophobic, cross-linked polystyrene divinyl benzene adsorbent resin. AMBERLITE XAD-16 has a macroreticular structure, with both a continuous polymer phase and a continuous pore phase. In a particularly preferred embodiment, the resin used in the present invention has a particle size ranging from 100-200 microns.

Other adsorbents, such as those in the AMBERLITE XAD adsorbent series which contain hydrophobic macroreticular resin beads, with particle sizes in the range of 100-200 microns, are also be effective in the methods of the present invention. Moreover, different variations of the AMBER-LITES, such as the AMERCHROM CG series of adsorbents, used with particle sizes in the range of 100-200 microns, may also be suitable for use in the present invention. The AMBER-LITE XAD-16 is preferred since it can be re-used many times (over 100 times). However, it is contemplated that for food, the use of governmentally-approved resins in the present invention may be considered important and/or desirable. Various geometries may be used for the purification, including batch adsorption, column chromatography, and the like, as known in the art.

The resins are washed, e.g. with water or an aqueous buffer to remove unbound material from the extract.

Any solvent can be used to remove the adsorbed ellagitannins. Preferred are lower alkanols containing 1 to 4 carbon atoms and most preferred is ethanol (ethyl alcohol) since it is approved for food use. Typically the ethanol is azeotroped with water; however, absolute ethanol can be used. Water containing malic acid and sugars in the pomegranate pass through the column. These may be collected and can be used in foods as flavors.

The eluted tannins are substantially purified relative to the starting material, and may be further purified, e.g. by chromatography, etc., or may be directly used in formulations of interest. The final composition may be concentrated, filtered, dialyzed, etc., using methods known in the art. For therapeutic applications, the tannins are administered to a mammal in a physiologically acceptable dosage form, including those that may be administered to a human orally, etc. as a bolus or by continuous infusion over a period of time. Alternative routes of administration include intramuscular, intraperitoneal, intra-cerobrospinal, subcutaneous, intra-articular, intra-synovial, intrathecal, topical, or inhalation routes.

Compositions

Compositions of interest are obtained from the above purification process. The compositions comprise ellagitannins and fractions thereof, as described below, and may be provided as a powder, in solution, e.g. in water or aqueous buffer, ethanol, etc. Solutions may also comprise pomegranate juice or other fruit juices and foods. Such compositions may comprise at least about 0.1% ellagitannins as either weight/volume or percentage of weight; usually at least about 10%, at least about 20% ellagitannins; more usually at least about 30% ellagitannins; and may comprise at least about 40% ellagitannins; at least about 50% ellagitannins; at least about 60% ellagitannins; or more. The identity of the ellagitannins may be confirmed using any suitable method, e.g. HPLC; etc.

Included in the compositions of the invention are extracts comprising punicalagin or gallagic acid which may be present as a component of total pomegranate tannins, or may be isolated from other tannins present in pomegranate extracts. Gallagic acid may be present at a concentration of at least about 0.1%, usually at least about 10%, at least about 20%, at least about 30%, or higher, up to and including a substantially pure composition of gallagic acid.

Included in the compositions of the invention are extracts comprising punicalagins which may be present as a component of the total tannins, or may be isolated from other tannins present in pomegranate extracts. Punicalagins may be present at a concentration of at least about 5%, at least about 10%, or more.

From the total tannins produced by the methods described above or by conventional methods, a pure composition of gallagic acid or punicalagin may be derived by chromatography. The total tannins are adsorbed onto a lipophilic column, e.g. a Sephadex-Lipophilic LH-20 column pre-equilibrated with an aqueous methanol solution, and eluted with increasing amounts of methanol. The resulting compounds are optionally dried and rechromatographed.

Included in the compositions of the invention are extracts comprising ellagic acid and ellagic acid glycosides, which may be present as a component of the total tannins, or may be isolated from other tannins present in pomegranate extracts. Ellagic acid and ellagic acid glycosides may be present at a concentration of at least about 5%, at least about 10%, or more.

Included in the compositions of the invention are extracts comprising anthocyanins and anthocyanidins, which may be present as a component of the total tannins, or may be isolated from other tannins present in pomegranate extracts. Anthocyanins and anthocyanidins may be present at a concentration of at least about –0.1%, at least about 5%, at least about 10%, or more.

Uses of Ellagatannins

The tannins obtained by the methods of the invention may be used to formulate pharmaceuticals, nutraceuticals, herbal medicines, food additive, cosmetics, beverages, etc. Herbal medicines of interest include, but not restricted to, active fractions from certain herbal preparations such as nettles (*Urtica dioica*)-turmeric (*Curcuma longa*), tea; marine or terrestial animal products, e.g. bioactive lipids from *Perna canaliculus, Dromaius nova hollandiae*, etc.

The extracts of the invention may be provided as a composition with a pharmaceutically acceptable carrier. Such dosage forms encompass physiologically acceptable carriers that are inherently non-toxic and non-therapeutic. Examples of such carriers include ion exchangers, soft gels, oils, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of tannins include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The extracts will typically be formulated in such vehicles at a concentration of about 0.1 µg/ml to 100 µg/ml and higher.

Nutraceutical formulations of interest include foods for veterinary or human use, including health food bars, drinks and drink supplements, and the like. These foods are enhanced by the inclusion of a biologically active extract of the invention. For example, in the treatment of chronic inflammatory diseases, such as arthritis, the normal diet of a patient may be supplemented by a nutraceutical formulation taken on a regular basis.

For cosmetic formulations, the compositions of the invention may optionally comprise skin benefit materials. These include estradiol; progesterone; pregnanalone; coenzyme Q10; methylsolanomethane (MSM); copper peptide (copper extract); plankton extract (phytosome); glycolic acid; kojic acid; ascorbyl palmitate; all-trans-retinol; azaleic acid; salicylic acid; broparoestrol; estrone; adrostenedione; androstanediols; etc. The steroids will generally present at a concentration of less than about 2% of the total by weight of the composition, while the other skin benefit materials may be present at higher levels, for example as much as 10 to 15%.

The compositions of the invention may comprise a cosmetically acceptable vehicle to act as a dilutant, dispersant or carrier, so as to facilitate its distribution when the composition is applied to the skin. Vehicles other than or in addition to water can include liquid or solid emollients, solvents, humectants, thickeners and powders.

The cosmetically acceptable vehicle will usually form from 0.1%, or 5% to 99.9%, preferably from 25% to 80% by weight of the composition, and can, in the absence of other cosmetic adjuncts, form the balance of the composition.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the inven-

EXPERIMENTAL

Example 1

Pomegranate (*Punica granatum* L.) fruits are widely consumed fresh and in the forms of juice, concentrate, wine and jam. Pomegranate husk, a by-product of the commercial industry, is an inexpensive and abundant source of hydrolyzable tannins called ellagitannins. Previous methods to isolate pomegranate tannins included labor intensive and time-consuming solid phase extractions by column chromatography and/or use of specialized instruments such as preparative-high performance liquid chromatography (HPLC). An LH-20 column was used to purify an aqueous extract of pomegranate husk to afford gallagic acid in substantial yields (5-10 g/Kg husk; time <2 h). Using analytical HPLC and tandem LC-ES/MS, evaluation showed that it contains the ellagitannin, gallagic acid (>85% purity w/w). Since pomegranate tannins are reported to show potent antioxidant, antiatherosclerotic and anticancer activities, this method can be used for the large-scale production of gallagic acid for in vitro and in vivo biological studies. This method is practical for industrial applications and could provide a low-cost means to use a currently underutilized food by-product to develop phytoceuticals with potential health benefits or to develop products for use in the cosmetic and food biopreservative industries.

In this study we report a rapid method to prepare gallagic acid in substantial yield and purity which can be used for in vitro and in vivo biological studies. This method has industrial applications since it can be easily scaled-up, and is cost-effective since its uses an inexpensive by-product of the commercial juice industry, pomegranate husk, which after pressing is currently used as cattle-feed. We also report the use of NMR spectroscopic methods and tandem LC-ES/MS in negative mode, to identify gallagic acid.

Reagents

All solvents were HPLC grade and purchased from Fisher Scientific Co. (Tustin, Calif.). Formic and acetic acids, Sephadex Lipophilic LH-20 and Amberlite XAD-16 resins were purchased from Sigma Aldrich Co. (St. Louis, Mo.).

General Experimental Procedures

Nuclear Magnetic Resonance (NMR) spectra were recorded on Bruker instruments operating at 400 MHz for $^1$H and 150 MHz for $^{13}$C. Chemical shifts for gallagic acid (1) were recorded in acetone-d6 and are in δ (ppm) relative to the solvent peaks. HPLC-ES/MS analyses were carried out on an LCQ Classic Finnigan LC-MS/MS system (ThermoFinnigan, San Jose, Calif.), equipped with a HP 1100 series HPLC system consisting of an autosampler/injector, quaternary pump, column heater, and diode array detector (DAD). Data handling was carried out using Xcalibur 1.2 software (Finnigan Corp). HPLC analyses were carried out on Waters Alliance 2690 system equipped with a photo diode array (PDA) detector (Waters Corp., Milford, Mass.) and data handling was with Waters Millenium v 3.02 software.

Pomegranate fruits were washed and cleaned to yield their husk and aril, separate from seeds and juice. The husk (1 Kg) was percolated with water (5 L), squeezed by hand, then instantly blended (Waring Blender, New Hartford, Conn., USA). The thick husk puree was filtered through cheesecloth and squeezed dry to yield a dark brown aqueous extract. The XAD-16 resin column was prepared for chromatography by pre-washing in methanol then pre-equilibrating in water for 12 h. The aqueous extract was divided into 200 mL portions and adsorbed onto a vacuum aspirated column of Amberlite XAD-16 resin (500 g). Each column was eluted with copious amounts of distilled water (4 L) until the sugary pale yellow eluate was clear in color. Remaining water was removed from the resin by vacuum aspiration and the adsorbed tannins were eluted with MeOH (2×400 mL) to yield a dark brown solution. The time taken to complete one cycle per column was <15 min. Methanol was removed by a Rota-vap (Buchi) in vacuo at low temperature (37° C.) to yield pomegranate tannins as a dark brown powder (60 g/Kg fresh weight of husk).

The total pomegranate tannins (TPT) extract (1 g) purified from fruit peels was suspended in 10 mL of water and adjusted to pH 10 using 1M NaOH solution and kept at room temperature for 10 min. The mixture was neutralized with 1M HCl to pH 7. The solvent was removed under vacuum at 4° C., and the residue was suspended into 10 mL of MeOH and filtered and a residue (R1) and a filtrate (F1) were obtained. The residue (R1) was dissolved into 5 mL MeOH/water and subjected to Sephadex LH-20 column eluting with MeOH/water gradient. Twelve fractions were obtained (20 mL each). The fractions condensed with gallagic acid were combined and subjected to C18 column separation eluting with MeOH/water gradient. Fraction 6 was identified as pure form of gallagic acid by LC/MS analysis of one peak with MW 602.

HPLC conditions for analyses and quantification. All samples (50 μL injection volume) were filtered (0.22 μm) and analyzed on a Novapak (Waters Corp.) C-18 column, 150×3.9 mm i.d., 5 μm. The mobile phase, solvent A (2% $CH_3COOH$/$H_2O$) and solvent B (2% aqueous $CH_3COOH$/MeOH) was used under linear gradient conditions starting with 99% A for 5 min to 40% A over 40 min, hold time, 5 min with a flow rate of 1.0 mL/min. All compounds were detected at 254 nm, and at 378 nm (gallagic acid or other ellagitannins) and 366 nm (ellagic acid) for quantification. Pure isolated gallagic acid (1) (2 mg) was accurately weighed and dissolved in $H_2O$:MeOH (1:1, v/v) then serially diluted to afford 0.20, 0.10, 0.05 and 0.025 mg/mL concentrations, respectively. Ellagic acid (4) (1 mg) was dissolved in DMSO and serially diluted to afford 0.02, 0.01, 0.005 and 0.0025 mg/mL concentrations, respectively. Each sample was injected in duplicate and calibration curves were obtained by using their reponse factors (peak area/concentration). Pomegranate tannin extract (1 mg) was dissolved in $H_2O$:MeOH (1:1, v/v), and the mean area percentages of gallagic acid and ellagic acid peaks were used for quantification.

LC-ES/MS analyses. Conditions for detection of tannins were as follows: Column, Symmetery C-18, 100 mm×2.1 i.d., 3.5 μm, (Waters Corp., Milford, Mass.); Solvent A) 2% $HCOOH/H_2O$, B) 2% HCOOH/MeOH; gradient % A: initial: 99%, 30 min: 80%, 45 min: 60%, 60 min: 5%; run time 60 min; flow rate 0.15 mL/min; injection volume 20 μL; MS parameters: Ionization mode, electron spray (ES) negative mode; scan range: 120-1500 amu; scan rate: 1 scan/sec; cone voltage: 17 eV, source temperature: 275° C. Peak identities were obtained by matching their molecular ions (M-H$^+$) obtained by ES/MS and tandem MS with the expected theoretical molecular weights from literature data as: gallagic acid (1) (m/z 601)

Results and Discussion

Our chromatographic method utilizing LH-20 resin column can be accomplished quickly and produces a high yield of gallagic acid (time <1 h; 5-20 g/Kg husk) from fruit husk, a by-product of the commercial juice industry. The use of husk as starting material to produce gallagic acid is relevant since in the processing stages of the commercial juice industry, significant quantities of this water-soluble tannins are extracted from the fruit husk due to their hydrophilic properties when the fruits are hydrostatically pressed. This method is cost effective since it utilizes water and alcohols as eluants allowing the alcohols to be collected and recycled in subsequent resin columns to obtain the purified gallagic acid.

Gallagic acid purified from fruit husk was evaluated by analytical HPLC and tandem LC-ES/MS. Compound identities were confirmed by LC-ES/MS analyses where ion at M-H m/z 601 accounted for gallagic acid (1) as previously reported. NMR and MS-MS spectral analyses confirmed its identity. Punicalagin [2,3-(S)-hexahydroxydiphenoyl-4,6-(S, S)-gallagyl] can be considered to have a hexahydroxydiphenoyl moiety attached to gallagyl moiety.

In conclusion, we have developed a rapid new method to isolate large amounts of gallagic acid from fruit husk a major pomegranate tannin that is consumed by humans. Given the biological properties of pomegranate tannins as potent antioxidants and their effects on diseases such as atherosclerosis and cancer, this method could allow investigators access to large quantities of TPT for its potential use in appropriate in vivo models for health related studies. In addition, it would be feasible to scale-up this method, which may be practical for industrial applications. This could provide a low-cost means to use a currently underutilized food by-product to develop commercial products including new nutritional products with potential health benefits.

Example 2

Purification of Punicalagin

Total pomegranate tannins were extracted as described in Example 1.

Purification of Punicalagin (1) for quantification studies of TPT. Due to the unavailability of a commercial standard of punicalagin, the pure compound was isolated from TPT as follows. TPT (300 mg) was adsorbed onto a Sephadex-Lipophilic LH-20 column that was pre-equilibrated with $H_2O$:MeOH (8:2, v/v) and eluted with increasing amounts of MeOH. LC-ES/MS analyses revealed that the 50% MeOH fraction was enriched in two compounds, both corresponding to the molecular weight for punicalagin (M-H m/z 1083). This fraction (273 mg) was evaporated in vacuo and re-chromatographed, this time pre-equilibrating the column with EtOH. Elution with increasing amounts of $H_2O$ and $Me_2CO$ to EtOH:$H_2O$:$Me_2CO$ (6:3:1, v/v/v) and finally EtOH:$Me_2CO$ (1:1, v/v) yielded a fraction which was evaporated in vacuo to afford a yellow amorphous powder (34 mg). This was identified as a mixture of α- and β-punicalagin anomers by $^1H$ and $^{13}C$ NMR spectral data, which were consistent with literature reports.

HPLC conditions for analyses and quantification. All samples (50 μL injection volume) were filtered (0.22 μm) and analyzed on a Novapak (Waters Corp.) C-18 column, 150×3.9 mm i.d., 5 μm. The mobile phase, solvent A (2% $CH_3COOH$/$H_2O$) and solvent B (2% aqueous $CH_3COOH$/MeOH) was used under linear gradient conditions starting with 99% A for 5 min to 40% A over 40 min, hold time, 5 min with a flow rate of 1.0 mL/min. All compounds were detected at 254 nm, and at 378 nm (punicalagins) and 366 nm (ellagic acid) for quantification. Pure isolated punicalagin (1) (2 mg) was accurately weighed and dissolved in $H_2O$:MeOH (1:1, v/v) then serially diluted to afford 0.20, 0.10, 0.05 and 0.025 mg/mL concentrations, respectively. Ellagic acid (4) (1 mg) was dissolved in DMSO and serially diluted to afford 0.02, 0.01, 0.005 and 0.0025 mg/mL concentrations, respectively. Each sample was injected in duplicate and calibration curves were obtained by using their reponse factors (peak area/concentration). TPT (1 mg) was dissolved in $H_2O$:MeOH (1:1, v/v), and the mean area percentages of the punicalagin (two individual peaks corresponding to α- and β-anomers) and ellagic acid peaks were used for quantification.

LC-ES/MS analyses. Conditions for detection of tannins were as follows: Column, Symmetery C-18, 100 mm×2.1 i.d., 3.5 μm, (Waters Corp., Milford, Mass.); Solvent A) 2% HCOOH/$H_2O$, B) 2% HCOOH/MeOH; gradient % A: initial: 99%, 30 min: 80%, 45 min: 60%, 60 min: 5%; run time 60 min; flow rate 0.15 mL/min; injection volume 20 μL; MS parameters: Ionization mode, electron spray (ES) negative mode; scan range: 120-1500 amu; scan rate: 1 scan/sec; cone voltage: 17 eV, source temperature: 275° C. Peak identities were obtained by matching their molecular ions (M-H$^+$) obtained by ES/MS and tandem MS with the expected theoretical molecular weights from literature data as: punicalagin (1) (m/z 1083); punicalin (2) (m/z 781; M-hexahydroxyphenoyl moiety); gallagic acid (3) (m/z 601) and ellagic acid (4) (m/z 301) [1,2,9]. Ellagic acid derivatives correlated with literature and were identified as ellagic acid hexoside (m/z 463), ellagic acid rhamnoside (m/z 447) and ellagic acid pentoside (m/z 433).

Results and Discussion

Figure 2:
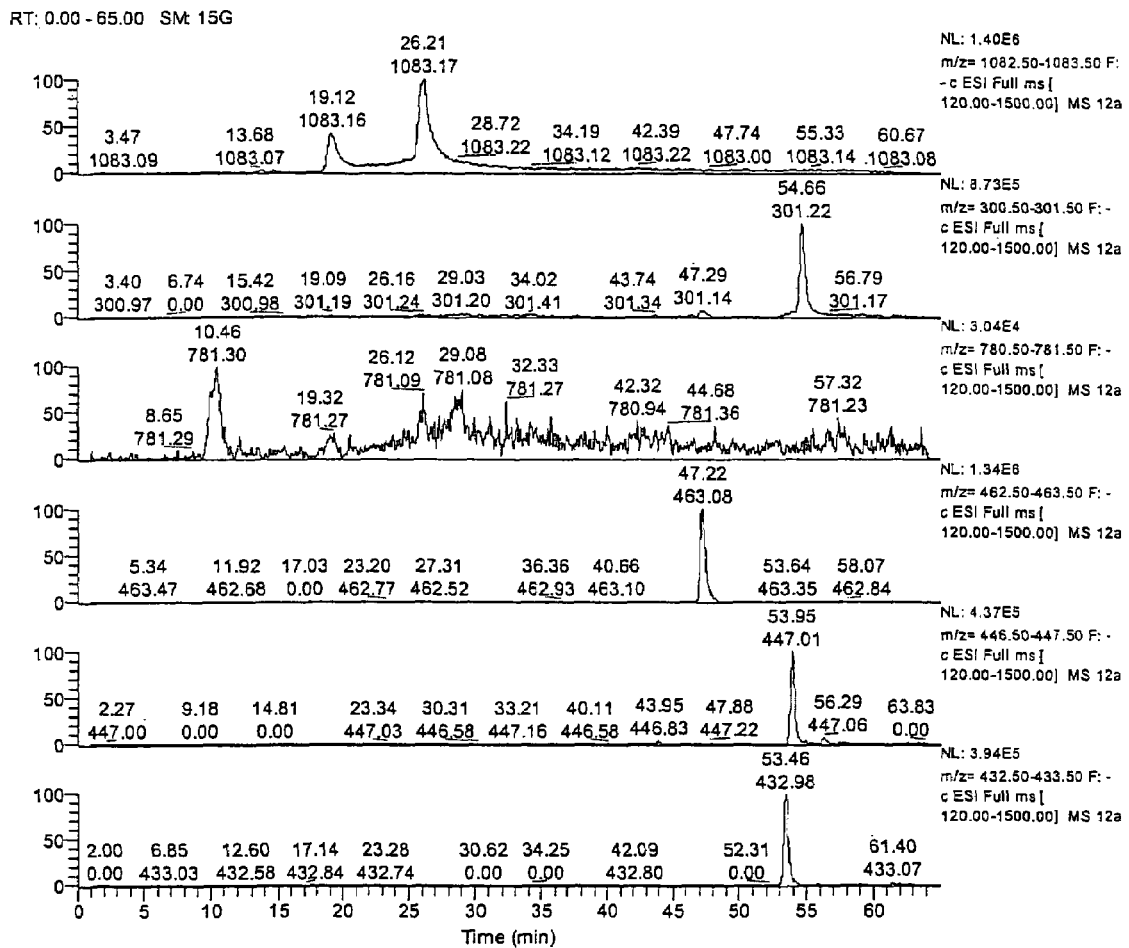
FIG. 2. LCMS spectra of total pomegranate tannins (TPT) showing extracted ion chromatograms of punicalagin isomers, m/z 1083; ellagic acid, m/z 301; punicalin, m/z 781; ellagic acid hexoside, m/z 463; ellagic acid rhamnoside, m/z 447; ellagic acid pentoside, m/z 433; as previously reported (1). Spectra were obtained by electrospray (ES) ionization in negative mode acquiring ions between 120-1500 amu.
Figure 3A:
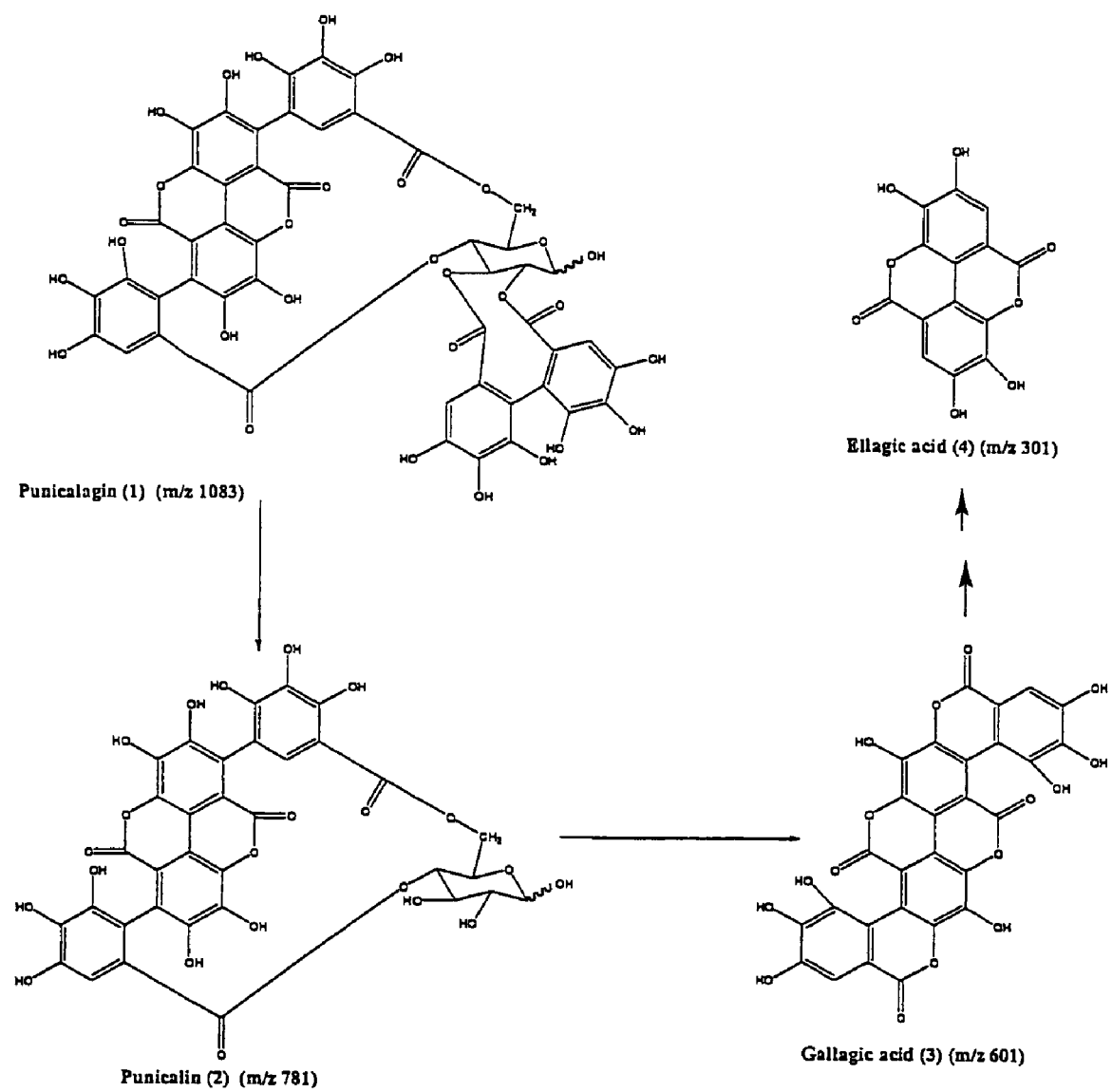
FIG. 3A: Scheme showing chemical structure of punicalagins (1), punicalin (2), gallagic acid (3) and ellagic acid (4) related to their mass spectral information.
Figure 3B:
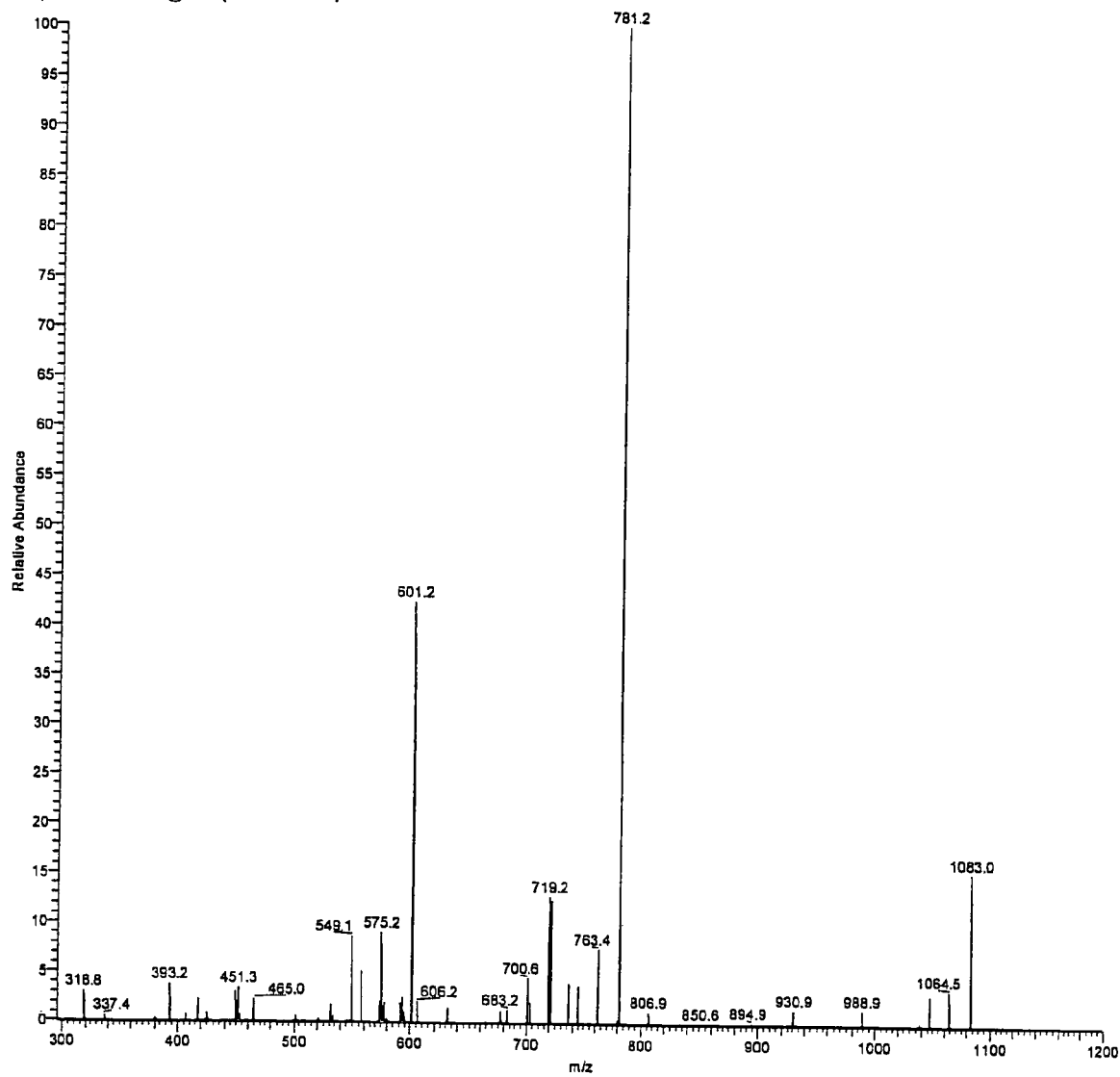
FIG. 3B: MS-MS spectra by direct infusion of punicalagin (m/z 1083) by shows the subsequent loss of hexahydroxydiphenoyl moiety to give punicalin (m/z 781) and then hexose to give gallagic acid (m/z 601).

TPT purified from fruit husk was evaluated by analytical HPLC (FIG. 1A) and tandem LC-ES/MS (FIGS. 2 and 3). Compound identities were confirmed by LC-ES/MS analyses where two ions at M-H m/z 1083 accounted for the α- and β-anomers of punicalagin (1) as previously reported. The minor compounds in TPT were ellagic acid (4) (M-H m/z 301), punicalin (2) (M-H m/z 781) and ellagic acid glycosides (hexoside, M-H m/z 463; rhamnoside, M-H m/z 447 and pentoside, M-H m/z 433) corresponding to the previous reports (FIG. 2).

Figure 1B:
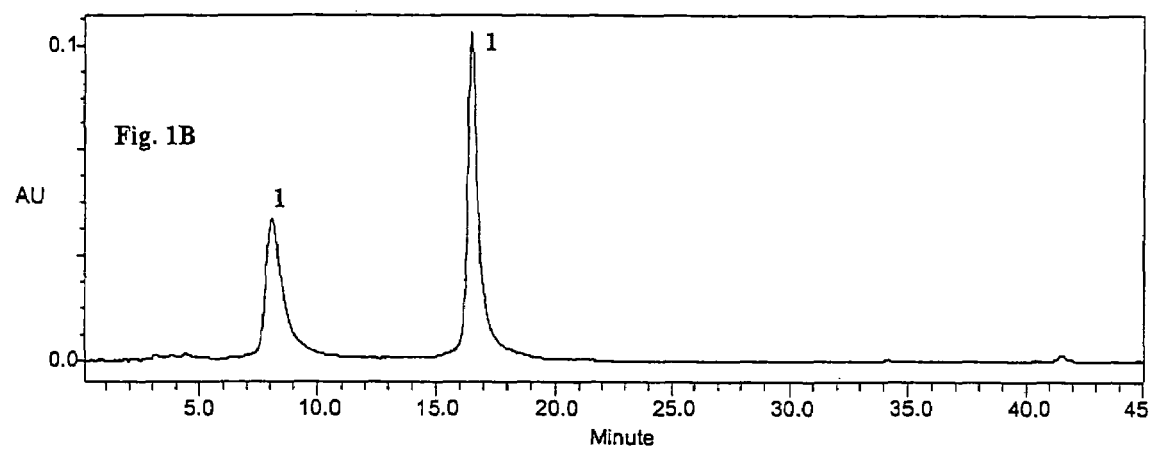
FIG. 1B: HPLC chromatogram of pure punicalagin anomers isolated from TPT.
Figure 1C:
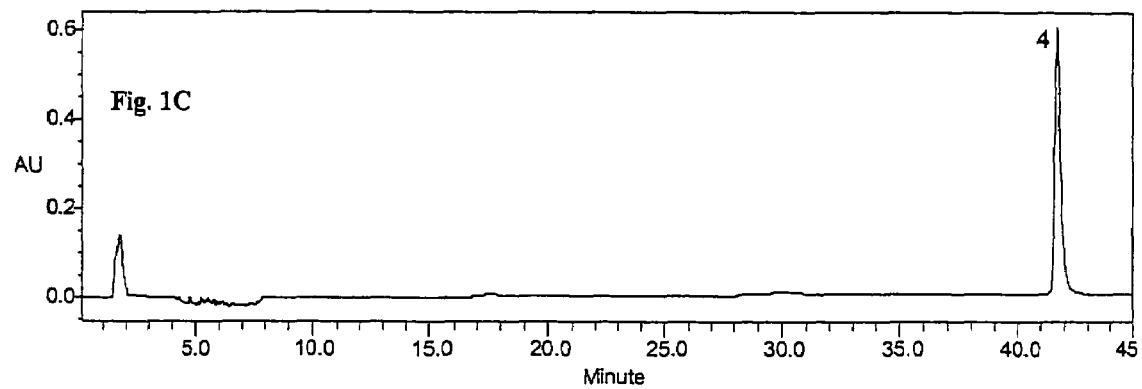
FIG. 1 C: HPLC chromatogram of commercially available ellagic acid. HPLC-UV detection wavelengths for quantification of punicalagins and ellagic acid in TPT were 378 nm and 366 nm, respectively.

Quantification studies on TPT were conducted using isolated punicalagin anomers (1) (FIG. 1B) whose NMR and MS-MS spectral analyses confirmed its identity and a commercially available sample of ellagic acid (4) (FIG. 1C). TPT contains 85% w/w of punicalagin anomers and 1.3% w/w ellagic acid. The $^{13}C$ NMR spectrum of the punicalagin isolated from TPT, revealed the two anomeric carbons at δ90.2 and δ94.4 corresponding to α- and β-punicalagin, respectively. Punicalagin [2,3-(S)-hexahydroxydiphenoyl-4,6-(S, S)-gallagyl-D-glucose] can be considered to have a hexahydroxydiphenoyl moiety attached to gallagylglucose (punicalin). MS-MS studies of punicalagin (1) at M-H m/z 1083 showed ions corresponding to punicalin (2) at M-H m/z 781, gallagic acid (3) at M-H m/z 601 and ellagic acid (4) at M-H m/z 301 as shown in FIGS. 3A and B.

Example 3

Tannins are plant polyphenols divided into two chemically and biologically distinct groups: condensed tannins (proanthocyanidins) and hydrolyzable tannins (ellagitannins and gallotannins). Proanthocyanidins are also referred to as catechuic tannins and are common to tea and fruits that include cranberries, bilberries, blueberries and grapes. Ellagitannins consist of polymers of glucose and ellagic acid, gallic acid and/or hexahydroxydiphenic acids common to fruits including raspberries, strawberries and pomegranates.

Compounds present in pomegranate husk include the major ellagitannin, punicalagin and its isomers [2,3-hexahydroxydiphenoyl-4,6-gallagylglucose] (1), as well as lesser amounts of punicalin [4,6-gallagylglucose] (2), gallagic acid (3) and ellagic acid (4) and its glycosides (ellagic acid hexoside, pentoside, rhamnoside etc.). Commercial pomegranate juices exhibit potent antioxidant properties attributed to their high content of hydrolyzable tannins including the punicalagin isomers which can reach levels >2 g/L juice, depending on the fruit cultivar and processing methods. The superior antioxidant activity of the punicalagins has been correlated to its hexahydroxydiphenoyl moiety and large number of hydroxyl (—OH) groups in its highly oxidized structure (1). Tannins have also been identified as the active compounds in pomegranate juice responsible for the ability of this juice to protect human low-density lipoprotein cholesterol from oxidation in vivo, which is a key step in the pathogenesis of atherosclerosis.

Materials and Methods

Reagents. All solvents were HPLC grade and purchased from Fisher Scientific Co. (Tustin, Calif.). Ellagic, formic and acetic acids, Sephadex Lipophilic LH-20 and Amberlite XAD-16 resins were purchased from Sigma Aldrich Co. (St. Louis, Mo.).

General Experimental Procedures. NMR spectra were recorded on Bruker instruments operating at 400 MHz for $^1$H and 150 MHz for $^{13}$C. Chemical shifts for punicalagin (1) were recorded in acetone-d6 and are in δ (ppm) relative to the solvent peaks. HPLC-ES/MS analyses were carried out on an LCQ Classic Finnigan LC-MS/MS system (ThermoFinnigan, San Jose, Calif.), equipped with a HP 1100 series HPLC system consisting of an autosampler/injector, quaternary pump, column heater, and diode array detector (DAD). Data handling was carried out using Xcalibur 1.2 software (Finnigan Corp). HPLC analyses were carried out on Waters Alliance 2690 system equipped with a photo diode array (PDA) detector (Waters Corp., Milford, Mass.) and data handling was with Waters Millenium v 3.02 software.

Purification of Total Pomegranate Tannins (TPT). Seventeen fresh pomegranate fruits (Ruby River, Lot #3127) were purchased (Whole Foods Supermarket, Westwood, LA, Calif.), washed and cleaned to yield their husk and aril, separate from seeds and juice. The husk (1 Kg) was percolated with water (5 L), squeezed by hand, then instantly blended (Waring laboratory heavy duty blender, New Hartford, Conn., USA). The thick husk puree was filtered through cheesecloth and squeezed dry to yield a dark yellow aqueous extract and residue which was discarded. A 2 L aliquot of the aqueous extract was divided into 200 mL portions and adsorbed onto a gravity column of Amberlite XAD-16 resin (500 g) which was pre-equilibrated in water. Each column was eluted with copious amounts of distilled water (4 L) until the sugary pale yellow eluate was clear in color. The column was allowed to run dry and remaining water was removed from the resin by vacuum aspiration. The adsorbed tannins were eluted with MeOH (or EtOH; 2×400 mL) to yield a dark yellow solution. Solvent was removed in vacuo to yield total pomegranate tannins (TPT) as a dark brown powder (16.5 g).

Purification of Punicalagin (1). TPT (300 mg) was adsorbed onto a Sephadex-Lipophilic LH-20 column that was pre-equilibrated with $H_2O$:MeOH (8:2, v/v) and eluted with increasing amounts of MeOH. LC-ES/MS analyses revealed that the 50% MeOH fraction was enriched in two compounds, both corresponding to the molecular weight for punicalagin (M-H m/z 1083). This fraction (273 mg) was evaporated in vacuo and re-chromatographed, this time pre-equilibrating the column with EtOH. Elution with increasing amounts of $H_2O$ and $Me_2CO$ to EtOH:$H_2O$:$Me_2CO$ (6:3:1, v/v/v) and finally EtOH:$Me_2CO$ (1:1, v/v) yielded a yellow amorphous powder (34 mg). This was identified as a mixture of α- and β-punicalagin anomers by $^1$H and $^{13}$C NMR spectral data which were consistent with literature (7, 12).

HPLC conditions for analyses and quantification. All samples (50 μL injection volume) were filtered (0.22 μm) and analyzed on a Novapak (Waters Corp.) C-18 column, 150×3.9 mm i.d., 5 μm. The mobile phase, solvent A (2% $CH_3COOH$/$H_2O$) and solvent B (2% aqueous $CH_3COOH$/MeOH) was used under linear gradient conditions starting with 99% A for 5 min to 40% A over 40 min, hold time, 5 min with a flow rate of 1.0 mL/min. All compounds were detected at 254 nm, and at 378 nm (punicalagins) and 366 nm (ellagic acid) for quantification. Pure isolated punicalagin (1) (2 mg) was accurately weighed and dissolved in $H_2O$:MeOH (1:1, v/v) then serially diluted to afford 0.20, 0.10, 0.05 and 0.025 mg/mL concentrations, respectively. Ellagic acid (4) (1 mg) was dissolved in DMSO and serially diluted to afford 0.02, 0.01, 0.005 and 0.0025 mg/mL concentrations, respectively. Each sample was injected in duplicate and calibration curves were obtained by using their reponse factors (peak area/concentration). TPT (1 mg) was dissolved in $H_2O$:MeOH (1:1, v/v), and the mean area percentages of the punicalagin (two individual peaks corresponding to α- and β-anomers) and ellagic acid peaks were used for quantification.

LC-ES/MS analyses. Conditions for detection of tannins were as follows: Column, Symmetery C-18, 100 mm×2.1 i.d., 3.5 μm, (Waters Corp., Milford, Mass.); Solvent A) 2% HCOOH/$H_2O$, B) 2% HCOOH/MeOH; gradient % A: initial: 99%, 30 min 80%, 45 min: 60%, 60 min: 5%; run time 60 min; flow rate 0.15 mL/min; injection volume 20 μL; MS parameters: Ionization mode, electron spray (ES) negative mode; scan range: 120-1500 amu; scan rate: 1 scan/sec; cone voltage: 17 eV. Peak identities were obtained by matching their molecular ions (M-H$^+$) obtained by ES/MS and tandem MS with the expected theoretical molecular weights from literature data as: punicalagin (1) (m/z 1083); punicalin (2) (m/z 781; M-hexahydroxyphenoyl moiety); gallagic acid (3) (m/z 601; punicalin-hexose-2CO) and ellagic acid (4) (m/z 301) (1,2,7). Ellagic acid derivatives correlated with literature (1,2) and were identified as ellagic acid hexoside (m/z 463), ellagic acid rhamnoside (m/z 447) and ellagic acid pentoside (m/z 433).

Total pomegranate tannins (TPT) purified from fruit husk was evaluated by analytical HPLC (FIG. 1A) and tandem LC-ES/MS (FIGS. 2 and 3). The HPLC chromatogram revealed predominant peaks corresponding to the retention times of pure isolated punicalagin anomers (1) (FIG. 1B) and a commercially available sample of ellagic acid (4) (FIG. 1C). Compound identities were confirmed by LC-ES/MS analyses with both punicalagin anomers at m/z 1083 and ellagic acid at m/z 301, corresponding to literature (FIG. 2). The minor compounds in TPT were identified by LC-ES/MS as punicalin (2) at m/z 781 and ellagic acid glycosides: hexoside, m/z 463; rhamnoside, m/z 447 and pentoside, m/z 433, corresponding to the previous report (1) (FIG. 2).

Quantification studies on TPT showed that it contains 80% w/w of punicalagin anomers and 1.3% w/w ellagic acid. For quantification studies, pure punicalagin was isolated from TPT and NMR and MS-MS spectral analyses confirmed its identity, as previously reported. Punicalagin [2,3-(S)-hexahydroxydiphenoyl-4,6-(S,S)-gallagyl-D-glucose] can be considered to have a hexahydroxydiphenoyl moiety attached to gallagylglucose (punicalin). MS-MS studies of punicalagin (1) at m/z 1083 showed ions corresponding to punicalin (2) at m/z 781 (punicalagin less hexahydroxydiphenoyl fragment), gallagic acid (3) at m/z 601 and ellagic acid (4) at m/z 301 as shown in FIG. 3. As previously reported, punicalagin in solution rapidly interconverts to α- and β-anomers. The $^{13}$C NMR spectrum of punicalagin, isolated from TPT, revealed the two anomeric carbons at δ90.2 and δ94.4 corresponding to α- and β-punicalagin, respectively.

REFERENCES

M. I. Gil, F. A. Tomas-Barberan, B. Hess-Pierce, D. M. Holcroft, A. A. Kader, J. Agric. Food Chem. 48 (2000) 4581.
B. Cerda, J. J. Ceron, F. A. Tomas-Barberan, J. C. Espin, J. Agric. Food Chem. 51(2003) 3493.
B. Cerda, R. Llorach, J. J. Ceron, J. C. Espin, F. A. Tomas-Barberan, Eur. J. Nutr. 42, (2003) 18.
T. Okuda, in: O. Hajime (Ed.) International Conference on Food Factors: Chemistry and Cancer Prevention, Springer Publishers, Japan, 1995, p. 280.
M. Aviram, L. Dornfield, Atheroclerosis (2001) 195.
P. S. Negi, G. K. Jayaprakasha, B. S. Jena, Food Chemistry, 80 (2003) 393.
A. Vidal, A. Fallarero, B. Pena, A. Medina, B. Gra, F. Rivera, Y. Gutierrez, P. Vuorela, J. Ethnopharm. 89 (2003) 295.
A. Calbert, C. Morand, C. Manach, C. Cemesy, Biomed Pharmacother. 56 (2002) 276.
A. J. Doig, D. H. Williams, P. B. Oelrichs, L. Baczynskyj, J. Chem. Soc., Perkin Trans. 1 (1990) 2317.
L. J. Filippich, J. Zhu, M. T. Asalami, Res. Vet. Sci. 50 (1991) 170.
S. A. A. El-Toumy, H. W. Rauwald, Phytochemistry 61 (2002) 971.
T. Tanaka, G-I. Nonaka, I. Nishioka, Chem Pharm. Bull. 34 (1986) 650.
T. Tanaka, G-I. Nonaka, I. Nishioka, Chem Pharm. Bull. 34 (1986) 656.

What is claimed is:

1. A composition comprising a total pomegranate tannins (TPT) extract, the TPT extract including punicalagin at a concentration of at least about 0.2% on a weight/weight basis.

2. The composition of claim 1, the composition being a nutraceutical formulation for ingestion by a human being or a non-human animal.

3. The composition of claim 2, the composition being for cardiovascular health.

4. The composition of claim 1, wherein said punicalagin is at a concentration of at least about 5%.

5. The composition of claim 4, the composition being a nutraceutical formulation for ingestion by a human being or a non-human animal.

6. The composition of claim 5, the composition being for cardiovascular health.

7. The composition of claim 1, wherein said punicalagin is at a concentration of at least about 10%.

8. The composition of claim 7, the composition being a nutraceutical formulation for ingestion by a human being or a non-human animal.

9. The composition of claim 8, the composition being for cardiovascular health.

10. The composition of claim 1, wherein said punicalagin is at a concentration of at least about 30%.

11. The composition of claim 10, the composition being a nutraceutical formulation for ingestion by a human being or a non-human animal.

12. The composition of claim 11, the composition being for cardiovascular health.

13. The composition of claim 1, wherein said punicalagin is at a concentration of at least about 50%.

14. The composition of claim 13, the composition being a nutraceutical formulation for ingestion by a human being or a non-human animal.

15. The composition of claim 14, the composition being for cardiovascular health.

16. The composition of claim 1, wherein said punicalagin is at a concentration of at least about 70%.

17. The composition of claim 16, the composition being a nutraceutical formulation for ingestion by a human being or a non-human animal.

18. The composition of claim 17, the composition being for cardiovascular health.

19. The composition of claim 1, wherein said punicalagin is at a concentration of at least about 90%.

20. The composition of claim 19, the composition being nutraceutical formulation for ingestion by a human being or a non-human animal.

21. The composition of claim 20, the composition being for cardiovascular health.

* * * * *

UNITED STATES PATENT AND TRADEMARK OFFICE
CERTIFICATE OF CORRECTION

| | | |
|---|---|---|
| PATENT NO. | : 7,638,640 B2 | Page 1 of 1 |
| APPLICATION NO. | : 11/395447 | |
| DATED | : December 29, 2009 | |
| INVENTOR(S) | : Navindra P. Seeram | |

It is certified that error appears in the above-identified patent and that said Letters Patent is hereby corrected as shown below:

In column 1 line 49: "purifications" should be --purification is--

In column 14 Claim 20, line 37: "being" should be --being a--

Signed and Sealed this

Twenty-ninth Day of June, 2010

David J. Kappos
*Director of the United States Patent and Trademark Office*